United States Patent
Hussain et al.

(10) Patent No.: US 8,680,347 B2
(45) Date of Patent: Mar. 25, 2014

(54) PREPARATION OF HIGH ASSAY DECABROMODIPHENYLALKANE PRODUCT WITH LOW OCCLUDED FREE BROMINE CONTENT

(75) Inventors: Saadat Hussain, Baton Rouge, LA (US); Arthur G. Mack, Prairieville, LA (US)

(73) Assignee: Albemarle Corporation, Richmond, VA (US)

( * ) Notice: Subject to any disclaimer, the term of this patent is extended or adjusted under 35 U.S.C. 154(b) by 33 days.

(21) Appl. No.: 13/383,174

(22) PCT Filed: Jul. 15, 2010

(86) PCT No.: PCT/US2010/042110
§ 371 (c)(1),
(2), (4) Date: Jan. 9, 2012

(87) PCT Pub. No.: WO2011/016966
PCT Pub. Date: Feb. 10, 2011

(65) Prior Publication Data
US 2012/0116132 A1    May 10, 2012

Related U.S. Application Data

(60) Provisional application No. 61/228,865, filed on Jul. 27, 2009.

(51) Int. Cl.
C07C 17/12    (2006.01)
(52) U.S. Cl.
USPC ........................................................ 570/206
(58) Field of Classification Search
None
See application file for complete search history.

(56) References Cited

U.S. PATENT DOCUMENTS

| | | | |
|---|---|---|---|
| 3,285,965 A | 11/1966 | Jenkner | |
| 3,752,856 A | 8/1973 | Nagy et al. | |
| 3,833,674 A | 9/1974 | Brackenridge | |
| 3,965,197 A | 6/1976 | Stepniczka | |
| 4,521,633 A | 6/1985 | Pedjac | |
| 4,847,428 A | 7/1989 | Gu | |
| 5,003,117 A | 3/1991 | Hussain | |
| 5,008,477 A | 4/1991 | Hussain | |
| 5,030,778 A * | 7/1991 | Ransford | 570/208 |
| 5,055,235 A | 10/1991 | Brackenridge et al. | |
| 5,077,334 A | 12/1991 | Hussain | |
| 5,124,496 A | 6/1992 | Templeton et al. | |
| 5,136,107 A | 8/1992 | Stephens et al. | |
| 5,302,768 A | 4/1994 | Hussain | |
| 5,324,874 A | 6/1994 | Ransford et al. | |
| 5,401,890 A | 3/1995 | Parks | |
| 5,457,248 A | 10/1995 | Mack et al. | |
| 5,741,949 A | 4/1998 | Mack | |
| 6,008,283 A | 12/1999 | Rose et al. | |
| 6,518,468 B1 | 2/2003 | Parks et al. | |
| 6,603,049 B1 | 8/2003 | Parks et al. | |
| 6,768,033 B2 | 7/2004 | Parks et al. | |
| 6,841,702 B2 | 1/2005 | Magdolen et al. | |
| 6,958,423 B2 | 10/2005 | Parks et al. | |
| 6,974,887 B2 | 12/2005 | Parks et al. | |
| 7,129,385 B2 | 10/2006 | Dawson et al. | |
| 7,408,088 B1 | 8/2008 | McKinnie | |
| 7,851,662 B2 | 12/2010 | McKinnie | |
| 7,994,373 B2 | 8/2011 | Hussain et al. | |
| 2003/0144563 A1 | 7/2003 | Falloon et al. | |
| 2004/0110996 A1 | 6/2004 | Parks et al. | |
| 2005/0118080 A1 | 6/2005 | Falloon et al. | |
| 2005/0222473 A1 | 10/2005 | Parks et al. | |
| 2005/0234271 A1 | 10/2005 | Parks et al. | |
| 2007/0088184 A1 | 4/2007 | Parks et al. | |
| 2008/0194889 A1 | 8/2008 | McKinnie | |
| 2008/0227903 A1 | 9/2008 | Hussain et al. | |

FOREIGN PATENT DOCUMENTS

| | | |
|---|---|---|
| CA | 1321213 C | 8/1993 |
| CA | 2094469 C | 2/1994 |
| CN | 1429800 A | 7/2003 |
| DE | 2950877 A1 | 6/1981 |
| DE | 3326343 A1 | 1/1985 |
| DE | 3422673 A1 | 12/1985 |
| EP | 0107978 A1 | 5/1984 |
| EP | 0265150 B1 | 4/1988 |

(Continued)

OTHER PUBLICATIONS

Albemarle Corporation, XP002458574, Saytex 8010 Flame Retardant, Brochure, 2001, 2 pages.

(Continued)

Primary Examiner — Johann R Richter
Assistant Examiner — Medhanit Bahta
(74) Attorney, Agent, or Firm — James A. Jubinsky

(57) ABSTRACT

A high assay decabromodiphenylalkane product in which the alkylene group contains in the range of about 1-10 carbon atoms and has an occluded free bromine content of <500 ppm is prepared. The process comprises brominating, in a liquid phase reaction mixture, at least one $\alpha,\omega$-diphenylalkane having an alkylene group of 1-10 carbon atoms, with a limited excess of bromine, in the presence of an aluminum, aluminum halide or a ferric halide catalyst in which the original halogen atoms of such halides are chlorine atoms, bromine atoms, or both. The limited excess of bromine is such that the maximum excess amount of bromine used in conducting the reaction is about 20 mole % relative to the stoichiometric amount required to convert the amount of $\alpha,\omega$-diphenylalkane used to decabromodiphenylalkane. Crude high assay decabromodiphenylalkane product is prepared without use of heat treatment, oven ageing, or grinding or other forms of pulverization.

14 Claims, No Drawings

(56) References Cited

FOREIGN PATENT DOCUMENTS

| | | |
|---|---|---|
| EP | 0347116 A2 | 12/1989 |
| EP | 0445595 A2 | 9/1991 |
| EP | 0571859 A2 | 12/1993 |
| GB | 981833 | 1/1965 |
| GB | 1278603 | 6/1972 |
| GB | 1411524 | 10/1975 |
| GB | 2143521 A | 2/1985 |
| JP | 50018430 A | 2/1975 |
| JP | 52039639 | 3/1977 |
| JP | 52139033 | 11/1977 |
| JP | 53053629 | 5/1978 |
| JP | 53116332 | 10/1978 |
| JP | 54044623 A | 4/1979 |
| JP | 58222043 | 12/1983 |
| JP | 62004241 | 1/1987 |
| JP | 10158202 | 6/1998 |
| JP | 10175893 | 6/1998 |
| WO | 93/24434 A1 | 12/1993 |
| WO | 94/22978 A1 | 10/1994 |
| WO | WO 9608457 A1 * | 3/1996 |
| WO | 03/055832 A1 | 7/2003 |

OTHER PUBLICATIONS

Kirk-Othmer Encyclopedia of Chemical Technology, "Chromatography Liquid", John Wiley and Sons, Inc., pp. 440-468.

Knoppen, R., et al., "Decabromodiphenylethane", Acta Cryst., 2007, E63, pp. 0585-0586.

Yang, Ze-hui, et al., "Technological Progress in Catalytic Synthesis of Decabromodiphenyl Ether by Brominating Diphenyl Oxide with Bromine Chloride", XP008073599, Fine Chemicals, vol. 19(1), Jan. 2002, pp. 42-44, abstract only translated.

* cited by examiner

PREPARATION OF HIGH ASSAY DECABROMODIPHENYLALKANE PRODUCT WITH LOW OCCLUDED FREE BROMINE CONTENT

REFERENCE TO RELATED APPLICATIONS

This application is the National Stage of International Patent Appl. No. PCT/US2010/042110, filed on Jul. 15, 2010, which in turn claims the benefit of U.S. Provisional Patent Appl. No. 61/228,865, filed on Jul. 27, 2009, the disclosures of which are incorporated herein by reference.

TECHNICAL FIELD

This invention relates to preparing high assay decabromodiphenylalkane products that contain low amounts of occluded free bromine without need for heat treatment/oven ageing and grinding, or other forms of pulverization, of the crude product to effect reduction of occluded free bromine.

BACKGROUND

High assay decabromodiphenylethane, a.k.a. α,ω-bis(pentabromophenyl)ethane, is currently manufactured by the bromination of 1,2-diphenylethane in the presence of a large excess of bromine, using anhydrous aluminum chloride as the catalyst. The main reason for using such a large excess (usually 80%-150% stoichiometric excess) is that bromine not only acts as a reagent but also as a solvent which is required for effective mixing. Excess bromine is then recovered and recycled to the next batch. However, using such a large excess of bromine not only leads to the formation of certain unwanted impurities but also results in substantial amount of free bromine being trapped inside the particles during product formation. This free bromine which is trapped within the product particles, commonly referred to as occluded free bromine, must be removed from the crude product before it can be used as a flame retardant in plastics. It is preferred that decabromodiphenylethane, like all other flame retardants, should have no free bromine left in the particles. In practice, however, there is always some (200-300 ppm) that remains in the finished product. Although trapped bromine can be effectively removed from the particles by using recrystallization from solvents, such processing is commercially impractical for materials like decabromodiphenylethane, which has extremely poor solubility in nearly all organic solvents. For example, solubility of decabromodiphenylethane is about 0.2 wt % in dibromomethane at reflux (98° C.), about 0.9 wt % in refluxing chlorobenzene (130° C.). Another known technique for reducing occluded free bromine content is to grind, mill, or otherwise pulverize the product so that trapped bromine can be liberated and removed by solvent washing. Commercially, a high-melting flame retardant such as decabromodiphenylethane, is heated at high temperatures (280-300° C.) in order to reduce substantially the amount of free bromine trapped inside the particles as formed. In fact, free bromine is so tightly bound to the particles of decabromodiphenylethane that an extended period of time is typically required in order for the free bromine content to be reduced to the desired specification of less than 300 ppm (wt/wt). This high-temperature treatment of the crude decabromodiphenylethane product, coupled with an associated drying step, tends to add significantly to the overall cost of manufacturing this product and also leads to degradation in color.

BRIEF NON-LIMITING SUMMARY OF THE INVENTION

In an attempt to substantially reduce the cost of manufacturing decabromodiphenylethane product, a new, and significantly improved bromination process has been developed. This process utilizes a suitable solvent such as dibromomethane as the bromination medium, along with substantially reduced excess of bromine (e.g., 10-20% or less excess instead of 80-100% excess used commercially) to produce product of suitably high assay with potentially reduced levels of undesirable impurities and better color. Heat treatment (oven-aging) is not required because the amount of bromine trapped inside the particles is already very low and at least when the process is conducted on a laboratory scale, can be well within the preferred specification of 300 ppm or less. Indeed, it is anticipated that when conducted at an industrial plant scale, the process of this invention will yield a content of occluded free bromine of no more than 500 ppm or less, and under optimized conditions, 300 ppm or less. Elimination of the heat treatment step alone is expected to lead to significant cost reduction. This process can be used for the manufacture of flame retardants other than decabromophenylalkane products, such as decabromodiphenylether and tetradecabromodiphenoxybenzene.

Thus, provided by this invention is, among other things, a process for the preparation of a high assay decabromodiphenylalkane product in which the alkylene group contains in the range of 1 to about 10 carbon atoms and has an occluded free bromine content of no more than 500 ppm, which process comprises brominating, in a liquid phase reaction mixture, a feed stream comprising at least one α,ω-diphenylalkane in which the alkylene group contains in the range of 1 to about 10 carbon atoms, with a limited excess of bromine, in the presence of an aluminum, aluminum halide or a ferric halide catalyst in which the halogen atoms of such halides, as used in forming the charge thereof into said reaction mixture are chlorine atoms, bromine atoms, or both, said limited excess of bromine being such that the maximum excess amount of bromine used in conducting the reaction is about 20 mole % relative to the stoichiometric amount required to convert the amount of diphenylalkane used to decabromodiphenylalkane. Typically, the feed stream is a solution of such α,ω-diphenylalkane in a suitable inert solvent, such as a halogenated hydrocarbon in which the halogen is chlorine and/or bromine.

FURTHER DETAILED DESCRIPTION OF THE INVENTION

As used herein, including the claims, the term "high assay" means that decabromodiphenylalkane product as produced—without use of heat treatment, oven ageing, or grinding, milling, or other form of pulverization to reduce occluded free bromine content—comprises at least 97 area % of decabromodiphenylalkane as determined by gas chromatography (GC). A procedure for conducting such GC analysis is set forth hereinafter.

The term "limited excess of bromine" as used herein, including the claims, means that throughout at least 90% of the time the diphenylalkane reactant is being introduced into the reactor or reaction zone, whether as a solution or otherwise, there is an excess amount of bromine in the reaction mixture in the reactor or reaction zone, the amount of such excess being referred to elsewhere herein.

Typical diphenylalkanes which can be brominated pursuant to this invention can be represented by the formula:

where $C_6H_5$ is a phenyl group and R is an alkylene group containing in the range of 1 to about 10 carbon atoms. Preferred R groups are methylene, ethylene, and propylene (a.k.a. trimethylene), which give the preferred reactants diphenylmethane; 1,2-diphenylethane (commonly referred to as diphenylethane); and 1,3-diphenylpropane. Of these, 1,2-diphenylethane and 1,3-diphenylpropane are especially preferred reactants. Other substituted diphenylalkanes which may be utilized include 1,4-diphenylbutane, 1,5-diphenylpentane, and their homologs in which the alkylene group contains up to about 10 carbon atoms.

One key feature of this invention is to employ a limited excess of bromine relative to the stoichiometric amount required in forming the decabromodiphenylalkane product. Thus, 10 moles of bromine ($Br_2$) per mole of diphenylalkane constitutes the stoichiometric amount. Accordingly, the molar ratio of $Br_2$:diphenylalkane that is used in conducting the bromination reaction of this invention is no higher than about 12:1 (i.e., the maximum excess amount of bromine used in conducting the reaction is about 20 mole % relative to the stoichiometric amount required to convert the amount of diphenylalkane used to decabromodiphenylalkane). Desirably, this maximum excess is about 15 mole %, and even more desirably is about 10 mole %. Indeed, it is deemed possible to conduct the reaction with only a 5 mole % excess of bromine relative to the stoichiometric amount required to convert the amount of diphenylalkane used to decabromodiphenylalkane.

Commercial grades of $Br_2$ may be used in the process of this invention. Should the $Br_2$ contain impurities that would give the final product an off-color, then either the $Br_2$ should be treated to reduce its impurity content or the off-color product should be treated to improve its color. The $Br_2$ is conveniently treated by simple distillation techniques. The off-color product can be treated by washing it with an organic wash solvent after the product is recovered from the reaction mass but prior to its being dried. The organic wash solvent can be any suitable organic solvent such as methylene bromide, ethylene dichloride, carbon tetrachloride, xylene, toluene, benzene, acetone, methanol, etc. Preferably, the solvent used as this organic wash solvent should be the same solvent that is being used as the solvent in the bromination process itself.

The bromination process of this invention utilizes a suitable bromination catalyst such as an aluminum trihalide in which the halogen atoms are bromine atoms or chlorine atoms, or both. Active forms of aluminum such as aluminum turnings, aluminum powder, or aluminum foil can be used, but in this case the amount of bromine charged to the reaction should take into consideration the amount of bromine required to convert the free aluminum to aluminum tribromide. Other relatively strong bromination catalysts such as ferric bromide can be used, but because of potential color problems, aluminum trichloride and aluminum tribromide are preferably utilized in forming the catalyst charged to the reactor. Combinations of such catalysts can be used, if desired. The amount of catalyst charged is typically in the range of about 0.1 to about 5 mole %, based on the total moles of bromine employed in the process. Use of amounts of catalyst in the upper portion of the foregoing range, e.g., from about 0.75 to about 2.0 mole % based on the total moles of bromine employed in the process is desirable as such elevated amounts tend to improve the assay of the decabromodiphenylalkane product. Another preferred amount of catalyst is in the range of about 0.5 to about 1.5 mole %, based on the total moles of bromine employed in the process, which amount of catalyst minimizes the formation of undesired impurities without compromising the assay of the desired decabrominated diphenylalkane product. Still another preferred amount of catalyst is about 0.3 to about 1.0 mole %, based on the total moles of bromine employed in the process.

A variety of inert solvents can be used in forming the high assay decabrominated diphenylalkane products. Although dibromomethane is a preferred solvent because of its proven ability to produce a high quality, high assay product, other haloalkanes can be used. Non-limiting examples of suitable haloalkane solvents include bromochloromethane, 1,2-dichloroethane, perchloroethylene, 1,2-dibromoethane, or any other solvent which remains inert during this bromination.

Bromination temperatures used in the process are typically in the range of about 45 to about 98° C. and preferably in the range of about 60 to about 95° C. The bromination is typically conducted in the absence of light.

Bromination of diphenylalkanes pursuant to this invention is conducted such that the decabrominated diphenylalkane product has a GC assay of at least 97 area %, and preferably at least 98 area %, of decabromodiphenylalkane. It is particularly preferred to conduct the bromination such that the end product has a GC assay of at least 99 area % of the desired decabromodiphenylalkane. Thus, the addition of the feed solution will occur over a period of time sufficient to achieve product having such assay under the reaction conditions and with the components and amounts thereof being used. The addition rate of the feed solution is dependent upon the scale of the reaction and the ability to control the temperature and to handle the rate and volume of hydrogen bromide evolution. On a laboratory scale, the addition typically requires about 1 to about 10 hours while on a commercial scale, the expected addition period of the feed solution would typically involve about 4 to about 12 hours or longer.

While various modes of feeding the reaction components to the reactor can be used, two methods are deemed convenient as well as effective. One such feeding mode involves charging all of the limited excess of bromine and a portion of the inert solvent to the reactor. Typically, the catalyst is either charged along with the bromine and a portion of the inert solvent or is added to the reactor after completing the charge of the bromine and a portion of the inert solvent. Thereupon, the feed of the diphenylalkane along with the remainder of the solvent, desirably as a preformed solution, is initiated.

Another mode of feeding involves separately and concurrently portionwise feeding of (i) bromine and (ii) a solution of the diphenylalkane and a portion of the inert solvent into a reactor or reaction zone containing the catalyst and the remainder of the inert solvent. In this way the molar ratio of the bromine to diphenylalkane can be controlled so as to be substantially continuously at about the maximum molar ratio of $Br_2$:diphenylalkane selected for use in the process as these components come together in the reaction zone. The rate of these feeds and the amount of heat removal should be controlled so that excess of heat buildup and excessive HBr evolution do not occur.

Whatever the mode of feeding employed, the feed solution of the diphenylalkane and inert solvent will generally contain about 95 to about 55 wt % of the solvent with the balance being the diphenylalkane. As a general rule, the higher the molecular weight of the diphenylalkane, the higher should be the percentage of solvent within the foregoing range so that the reaction mixture remains stirrable.

The bromination reaction can be conducted under elevated pressures in order to assist in controlling reaction rate and to avoid purge of a portion of the bromine from the reaction zone caused by excessive rate of HBr evolution, should this be found necessary or desirable in any given situation.

A post reaction period following completion of the addition of the feed(s) to the reactor or reaction zone to ensure achievement of high yield of high assay product is typically provided. The length of this post reaction period (a.k.a., ride time) will vary depending upon the scale of reaction. On a laboratory scale, this period is typically in the range of about 0.5 to about 1.5 hours. In a commercial installation in which the process is conducted on a batch basis, the post reaction period will typically be in the range of about 1 to about 2 hours.

A typical laboratory scale bromination by the process of this invention typically involves charging the bromination reactor with a suitable solvent and bromine, followed by the addition of the catalyst. A 20-45 wt % solution of diphenylalkane in a suitable solvent, preferably dibromomethane, is then fed to the reactor sub-surface, at reflux, followed by a post-feed reaction time (approximately 30 minutes). The reaction slurry is then cooled to room temperature, washed with water and dried in the oven. No additional oven-aging at high temperature is performed. Suitable solvents for use in the process are those which are inert and thermally stable at the reaction conditions and that can be distilled or steam distilled away from the crude decabromodiphenylalkane product.

When conducted in a proper manner for producing high assay decabromodiphenylethane, the product is typically white or only slightly off-white in color. It is anticipated that other decabromodiphenylalkane products, especially high assay 1,3-(pentabromophenyl)propane (a.k.a., decabromodiphenylpropane) when produced pursuant to this invention will also have white or only slightly off-white coloration.

A recommended gas chromatographic method for assaying the decabromodiphenylalkane products, especially decabromodiphenylethane product produced pursuant to this invention is as follows: the gas chromatography is conducted on a Hewlett-Packard 5890 Series II gas chromatograph equipped with a flame ionization detector, a cool on-column temperature and pressure programmable inlet, and temperature programming capability. The column is a 12QC5 HTS capillary column, 12 meter, 0.15μ film thickness, 0.53 mm diameter, available from SGE, Inc., part number 054657. Conditions were: detector temperature 350° C.; inlet temperature 70° C.; helium carrier gas at 10 ml/min.; inlet pressure 4.0 psi, increasing at 0.25 psi/min. to 9.0 psig and holding at 9.0 psi until the end of the run; oven temperature 60° C. with heating at 12° C./min. to 350° C. and holding for 10 min.; and injection mode of cool on-column. Samples were prepared by dissolving, with warming, 0.003 grams in 10 grams of dibromomethane and injection of 2 microliters of this solution. The integration of the peaks was carried out using Target Chromatography Analysis Software from Thru-Put Systems, Inc. However, other and commercially available software suitable for use in integrating the peaks of a chromatograph may be used. Thru-Put Systems, Inc. is currently owned by Thermo Lab Systems, whose address is 5750 Major Blvd., Suite 200, Orlando, Fla. 32819. The address of SGE, Incorporated is 2007 Kramer Lane, Austin, Tex. 78758.

The following Examples are present for purposes of illustration. They are not intended to limit the generic invention to only the details set forth therein.

EXAMPLE 1

Preparation of Decabromodiphenylethane in a Solvent Using 10% Excess Bromine

A 250-mL round bottom flask was fitted with a mechanical stirrer, a digital thermal probe, a heating mantle, a 0° C. reflux condenser and a Teflon® resin dip-tube for sub-surface feeding. The reactor was charged with approximately 72 mL of dibromomethane solvent and 176 g (1.1 mole, 10% stoichiometric excess) of bromine. Aluminum bromide (1.8 g, 10 wt % based on 1,2-diphenylethane (DPE) charge, 0.61 mole %, based on total moles of bromine) was now added and stirred to make a solution. This solution was then heated to reflux (73° C.). Diphenylethane (18.2 g, 0.1 mole) was dissolved in 9 mL of dibromomethane in a separate reservoir (Erlenmeyer flask) and was then fed, sub-surface, to the refluxing $Br_2$, $CH_2Br_2$, $AlBr_3$ catalyst solution, by means of a peristaltic pump, over a period of 200 minutes. As more and bromine was used up by the reaction, the reaction temperature slowly approached that of dibromomethane solvent (98° C.). During the addition, therefore, the reaction temperature rose from about 73° C. at the start of addition to 96° C. at the end of addition. The reaction slurry was kept at reflux for the next 30 minutes during which time the reflux temperature rose to 98° C., indicating that all bromine was consumed. Although 10% excess bromine was utilized in the reaction, the excess is assumed to have slowly been lost to the scrubber with evolving HBr due to the reaction temperature being about 36-38° C. higher than the boiling point of bromine (59.9° C.). This kind of loss can be avoided by carrying the reaction out under nominal pressure. The reddish slurry was allowed to cool and stand overnight. Water (100 mL) was added to break up the catalyst, followed by about 2.18 g of 50% aqueous sodium hydroxide solution to dissolve the aluminum salts. The slurry was filtered and the wet cake was allowed to dry in air for 48 hours at ambient temperature to give 92.9 g, 95.5% of the desired product. Upon analysis, the product showed a free bromine content of 130 ppm and an ionic bromide content of 967 ppm. A GC analysis showed the product assay (measured by the Br-10 content) to be 98.30 area %.

EXAMPLE 2

Preparation of Decabromodiphenylethane in a Solvent Using 20% Excess Bromine

This run was made in a manner identical to that of Example 1 and using the same equipment, except that initial charge in the reactor consisted of 72 mL of dibromomethane and 62 mL (193.4 g, 1.20 mole, 20% excess) of bromine. Aluminum bromide (1.8 g, 0.56 mole % based on the total moles of bromine) was then added and the contents brought to reflux at 73° C. Diphenylethane (18.2 g, 0.1 mole, dissolved in 9 mL of methylene bromide) was fed, sub-surface to refluxing bromine/solvent/catalyst solution at 73-95° C., over a period of 197 minutes. This was followed by reflux for an additional 197 minutes, cooling, treatment with water and caustic as before, and then isolation by filtration. The cake was dried at 120° C. in an oven for 2.5 hr, to give 94.7 g of the final product. Analysis showed the assay of this product to be 98.65 area %. The material had a free bromine content of 408 ppm and the ionics were 472 ppm.

EXAMPLE 3

Preparation of Decabromodiphenylethane in a Solvent Using 20% Excess Bromine

This run represents essentially a repeat of the run of Example 1 above, except that the amount of catalyst again was increased to 20 wt % (1.12 mole % based on the total moles of bromine) while keeping the amount of bromine the same. The increased amount of catalyst was assumed to improve upon the assay. Performed in the same equipment and in an identical manner, the initial reactor charge consisted of 72 mL of dibromomethane solvent, 62 mL of bromine and 3.6 g of aluminum bromide catalyst. DPE solution (18.2 g DPE dissolved in 9 mL of dibromomethane solvent) was fed to the reactor over a period of 195 minutes, at 73-95° C. Usual work-up was performed except the cake, after initial filtration, was washed with dibromomethane (2×20 mL), caustic (120 of about 8% aqueous solution) and finally, with water (2×100 mL). Dried the cake in air for 30 minutes, then in the oven at 125° C. for four hours, to give 94.5 g of shiny crystalline-looking product. As analyzed by GC, the assay on this product was 99.62 area %. It contained 396 ppm of free bromine and 159 ppm of ionic bromide.

EXAMPLE 4

Preparation of Decabromodiphenylethane in a Solvent Using 10% Excess Bromine and 10 wt % Catalyst This run was made in a similar manner as that of Example 3 by keeping everything else the same except reducing the catalyst back to 10 wt % (0.56 mole %, based on the total moles of bromine) from 20 wt % used in Example 3. DPE solution was fed at 75-96° C., over a period of 185 minutes. The filter cake was washed sequentially with dibromomethane (3×25 mL), with a solution of 20 g of 50% aqueous sodium hydroxide in 100 mL water, and with water (2×100 mL). The product was dried in air for 30 minutes, then in an oven at 125° C. for four hours to give 92.2 g of product which had an assay of 99.33 area %. It was analyzed to contain 228 ppm of free bromine and 491 ppm of ionic bromide.

The results of Examples 1-4 are summarized in the Table in which "DDE" assay refers to the assay of the decabromodiphenylethane product.

TABLE

Data on DDE Product From the Solvent Process of this Invention

| Example | Excess $Br_2$, % | Catalyst, wt % | Catalyst, mole % | DDE assay, GC area % | Free $Br_2$, ppm | Ionic bromide, ppm |
|---|---|---|---|---|---|---|
| 1 | 10 | 10 | 0.61 | 98.3 | 130 | 967 |
| 2 | 20 | 10 | 0.56 | 98.65 | 408 | 472 |
| 3 | 10 | 20 | 1.12 | 99.6 | 396 | 159 |
| 4 | 10 | 10 | 0.56 | 99.33 | 228 | 491 |

The results listed in the Table demonstrate the utility of this process to make high assay decabromodiphenylethane product of white color, having 98-99.6% $Br_{10}$, and acceptable levels of free bromine, without the conventionally used high temperature heat treatment and without grinding or other forms of pulverization to form a product having an occluded free bromine content of <500 ppm and preferably <300 ppm. It can be appreciated, therefore, that among the demonstrated advantages of the process are that utilization of bromine per batch is substantially reduced, that conventional workup procedures to reduce occluded free bromine such as heat treatment and grinding, milling, or the like are rendered unnecessary, the amount of impurities such as free bromine and ionic bromide can be reduced, and the cost effectiveness of processing to produce decabromodiphenylalkanes is improved.

It is to be understood and appreciated that although no grinding, milling, or other forms of pulverization are used in order to reduce the occluded free bromine content to a value of <500 ppm and preferably <300 ppm, once the product has been prepared having such a low occluded free bromine content the product can thereafter be ground, milled, or pulverized in order to reduce the size of the product, the practice of the present invention having already been completed by producing the product having such low occluded free bromine content without use of grinding, milling, and/or other forms of pulverization. It is also to be understood and appreciated that the term "occluded free bromine" is synonymous with "occluded elemental bromine" or more simply, "occluded bromine" where bromine is $Br_2$.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Each and every patent or publication referred to in any portion of this specification is incorporated in tow into this disclosure by reference, as if fully set forth herein.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text taken in context clearly indicates otherwise.

The invention may comprise, consist or consist essentially of the materials and/or procedures recited herein.

This invention is susceptible to considerable variation in its practice. Therefore the foregoing description is not intended to limit, and should not be construed as limiting, the invention to the particular exemplifications presented hereinabove.

The invention claimed is:

1. A process for the preparation of a high assay decabromodiphenylalkane product which as produced has an occluded free bromine content of no more than 500 ppm, which process comprises brominating, in a liquid phase reaction mixture, at least one diphenylalkane in which the alkylene group contains in the range of 1 to about 10 carbon atoms,
with bromine,
in the presence of an aluminum, aluminum halide or a ferric halide catalyst in which the halogen atoms of such halides, as used in forming the charge thereof into said reaction mixture are chlorine atoms, bromine atoms, or both,
wherein an excess of bromine is used in the process and wherein the maximum excess amount of bromine used in the process is about 20 mole % relative to the stoichiometric amount required to convert the diphenylalkane to the decabromodiphenylalkane product,
wherein the temperature of the bromination reaction mixture is maintained in the range of about 45 to about 98° C. at least during the mixing of the bromine and the diphenylalkane, and whereby the high assay decabromodiphenylalkane product is prepared without use of procedures to reduce the occluded free bromine content.

2. A process as in claim 1 wherein a solution of the diphenylalkane in an inert solvent is fed into a reactor or reaction zone containing bromine, catalyst, and inert solvent.

3. A process as in claim 1 wherein feeds of (i) a solution of the diphenylalkane in an inert solvent and (ii) bromine are separately and concurrently fed into a reactor or reaction zone containing said catalyst and inert solvent.

4. A process as in claim 1 wherein the catalyst is an aluminum trihalide in which the halogen atoms are bromine atoms, chlorine atoms, or both, and wherein the amount of said catalyst charged is in the range of about 0.1 to about 5 mole % based on the total moles of bromine employed in the process.

5. A process as in claim 4 wherein the diphenylalkane selected for use in the process is 1,2-diphenylethane or 1,3-diphenylpropane, or both, wherein the catalyst selected for use in the process is aluminum chloride or aluminum bromide, or both, and wherein the amount of said catalyst charged is in the range of about 0.75 to about 2.0 mole % based on the total moles of bromine employed in the process.

6. A process as in claim 4 wherein the diphenylalkane selected for use in the process is 1,2-diphenylethane or 1,3-diphenylpropane, or both, wherein the catalyst selected for use in the process is aluminum chloride or aluminum bromide, or both, and wherein the amount of said catalyst charged is about 0.3 to about 1.0 mole %, based on the total moles of bromine employed in the process.

7. A process as in claim 1 wherein the amount of said catalyst charged is in the range of about 0.75 to about 2.0 mole % based on the total moles of bromine employed in the process.

8. A process as in claim 7 wherein said amount of said catalyst charged is in the range of about 0.5 to about 1.5 mole % based on the total moles of bromine employed in the process.

9. A process as in claim 7 wherein said amount of said catalyst charged is in the range of about 0.3 to about 1.0 mole % based on the total moles of bromine employed in the process.

10. A process as in claim 1 wherein said temperature of the bromination reaction mixture is maintained at about 60 to about 95° C. at least during the mixing of the bromine and the diphenylalkane.

11. A process as in claim 1 wherein the process is conducted on a batch basis, wherein a post reaction period following completion of the addition of the feed(s) is provided, and wherein the length of such period ranges from about 0.5 to about 2 hours.

12. A process as in claim 3 which comprises controlling the molar ratio of bromine to diphenylalkane so as to be substantially continuously at about the maximum molar ratio of bromine:diphenylalkane as these components come together in the reaction zone, whereby excess heat build-up and excess hydrogen bromide evolution do not occur.

13. A process as in claim 1 wherein the maximum excess amount of bromine used in the process is about 15 mole % relative to the stoichiometric amount required to convert the diphenylalkane to the decabromodiphenylalkane product.

14. A process as in claim 13 wherein the diphenylalkane is diphenylethane and the decabromodiphenylalkane product is a decabromoethane product.

* * * * *